(12) United States Patent
Sun et al.

(10) Patent No.: US 6,469,303 B1
(45) Date of Patent: Oct. 22, 2002

(54) NON-DISPERSIVE INFRARED GAS SENSOR

(75) Inventors: Hong T. Sun, Los Gatos; Peter C. Hsi, Fremont, both of CA (US)

(73) Assignee: Rae Systems, Inc., Sunnyvale, CA (US)

( * ) Notice: Subject to any disclaimer, the term of this patent is extended or adjusted under 35 U.S.C. 154(b) by 0 days.

(21) Appl. No.: 09/574,578

(22) Filed: May 17, 2000

(51) Int. Cl.⁷ .................................................. G01J 5/02
(52) U.S. Cl. .................. 250/343; 250/345; 250/339.12; 250/339.13; 250/338.3
(58) Field of Search .................. 250/343, 345, 250/339.12, 338.3, 339.13

(56) References Cited

U.S. PATENT DOCUMENTS

| | | | |
|---|---|---|---|
| 3,793,525 A | 2/1974 | Burch et al. | 123/212 |
| 3,811,776 A | 5/1974 | Blau, Jr. | 356/51 |
| 4,578,762 A | 3/1986 | Wong | 702/32 |
| 4,622,464 A * | 11/1986 | Sukigara | 250/343 |
| 4,694,173 A | 9/1987 | Wong | 250/343 |
| 5,026,992 A | 6/1991 | Wong | 250/343 |
| 5,136,332 A | 8/1992 | Johnson | 399/303 |
| 5,163,332 A | 11/1992 | Wong | 73/863.23 |
| 5,341,214 A * | 8/1994 | Wong | 250/343 |
| 5,444,249 A | 8/1995 | Wong | 250/343 |
| 5,464,983 A | 11/1995 | Wang | 250/343 |
| 5,650,624 A | 7/1997 | Wong | 250/338.5 |
| 5,721,430 A * | 2/1998 | Wong | 250/339.13 |
| 5,834,777 A | 11/1998 | Wong | 250/343 |
| 6,121,617 A * | 9/2000 | Hirayama et al. | 250/343 |

* cited by examiner

Primary Examiner—Georgia Epps
Assistant Examiner—M. Hasan
(74) Attorney, Agent, or Firm—Skjerven Morrill LLP

(57) ABSTRACT

An NDIR sensor includes a cylindrical metallic tube, a printed circuit board platform that fits into one end of the tube, a diffusion filter that fits into the opposite end of the tube, and an optical system. The optical system includes an infrared source on the platform, a mirror on the inner wall of the tube so as to reflect and focus the infrared light from the infrared source, and a detector assembly that receives the infrared light after reflection. The gas sensor may further include a partition between the infrared source and the detector assembly, a removable filter on the diffusion filter, connecting pins attached to the platform, and a sealing layer formed under the platform. The detector assembly includes a signal detector and a reference detector. A first and second bandpass filters are respectively formed on the signal and reference detectors.

46 Claims, 3 Drawing Sheets

NON-DISPERSIVE INFRARED GAS SENSOR

BACKGROUND OF THE INVENTION

1. Field of the Invention

The present invention relates to a gas sensor and particularly, to a gas detector that measures the concentration of a gas using a characteristic infrared absorption band of the gas.

2. Description of the Prior Art

The gas analyzer manufacturing industry has employed a number of gas-detecting techniques in their devices for detecting specific gases. The techniques can be categorized into non-interactive gas analysis and interactive gas analysis. The non-interactive gas analysis techniques include non-dispersive infrared (NDIR) and dispersive infrared (DIR) techniques. Both NDIR and DIR techniques utilize the principle that various gases exhibit substantial absorption at characteristic wavelengths in the infrared radiation spectrum. Thus, a gas analyzer using the NDIR technique often uses a narrow-band transmission filter to isolate a specific wavelength band of infrared light that corresponds to the absorption spectrum of a target gas. In contrast, a gas analyzer using the DIR technique typically includes a prism or diffraction grating to isolate a specific wavelength band.

The non-interactive gas analysis techniques, especially the NDIR technique, offer a number of advantages over interactive gas analysis techniques which often include electrochemical fuel cells, sintered semiconductor (tin oxide), or catalysts (platinum bead) that chemically interact with a target gas. The advantages of non-interactive analysis include fast detection response, gas detection specificity, long term measurement stability, reduced maintenance cost, and good sensitivity. Interactive gas sensors have several drawbacks. The interactive gas sensors can be poisoned or contaminated potentially causing malfunctions that can place human life at risk. Additionally, interactive gas sensors are not good at detecting a target gas because the reagent used to determine the concentration of the target gas may react with other gases that are present in a sample, resulting in a false concentration reading for the target gas.

Despite their functional superiority, the NDIR gas sensors were not initially popular due to their structural complexity and high manufacturing cost. However, over the past several decades, a large number of measurement techniques based upon the NDIR principle have been proposed and successfully demonstrated. An early NDIR gas analyzer included an infrared source, a motor-driven mechanical chopper to modulate the source, a pump to push or pull gas through a sample chamber, a narrow bandpass interference filter, a sensitive infrared detector, and an optical system that focuses the infrared energy from the source onto the detector. U.S. Pat. Nos. 3,793,525, 3,811,776, and 4,578,762, which are herein incorporated by references in their entireties, describe early NDIR gas analyzers. Although these NDIR gas analyzers performed well, their large size, structural complexity, and high manufacturing cost precluded their use in a number of applications.

U.S. Pat. Nos. 4,694,173 and 5,026,992, which are herein incorporated by references in their entireties, describe NDIR gas detection techniques that do not use any moving parts such as mechanical choppers. These NDIR gas sensors that are more rugged, compact, and cost-effective than earlier ones. An attempt to further reduce manufacturing cost and structural complexity produced a low-cost NDIR gas sensor that employs a diffusion-type gas sample chamber. This sensor is disclosed in U.S. Pat. No. 5,136,332, which is herein incorporated by reference in its entirety. The diffusion-type gas sample chamber eliminates expensive optics, mechanical choppers, and a pump for pushing or pulling the gas into the sample chamber.

U.S. Pat. No. 5,136,332, which is herein incorporated by reference in its entirety, advanced the idea of using waveguides or tubular sample chambers in NDIR gas sensors. A waveguide sample chamber has highly reflective inner walls that allow probing radiation emanating from an infrared source at one end of the sample chamber to undergo multiple reflections before reaching an infrared detector at the opposite end of the sample chamber. This NDIR technique does not require the use of any optical components other than a pair of infrared transmitting windows at the ends of the sample chamber.

This design works well for low-cost, rugged and relatively high performance NDIR gas sensors, but has several drawbacks. The simple optical transport mechanism that relies only on multiple reflections decreases the ability to focus radiation sharply on the detectors, resulting in poor signal-to-noise ratio and reducing gas detection sensitivity. Furthermore, this optical system design increases the size of the gas sensor because of the lack of optical focusing components that might shorten the sample chamber path length.

The NDIR gas sensors using waveguide sample chambers expanded the scope of applications and created new potential applications of NDIR gas sensors. Thus, the improvement of NDIR gas sensors continued. For example, U.S. Pat. No. 5,464,983, which is herein incorporated by reference in its entirety, discloses sensor temperature stability improvements. U.S. Pat. Nos. 5,650,624 and 5,721,430, which are herein incorporated by references in their entireties, disclose low-power passive NDIR gas sensors. U.S. Pat. Nos. 5,444,249 and 5,834,777, which are herein incorporated by references in their entireties, disclose NDIR gas sensors fabricated on a monolithic silicon chip.

One important feature for NDIR sensors that has long been overlooked is the intrinsic safety of operating NDIR gas sensors in an explosive environment. The infrared light source in an NDIR gas sensor could ignite a flammable gas inside the sensor. If the ignition escapes from the NDIR sensor, a wider explosion could occur. An intrinsically safe, portable NDIR sensor may open new application areas, such as underground tunnels and sewers, chemical plants, and oil refineries.

SUMMARY OF THE INVENTION

An aspect of the present invention provides an NDIR sensor with an efficient configuration. The sensor includes a metallic tube, a platform that fits into the bottom end of the tube, a diffusion filter that fits into a top end of the tube, and an optical system on the platform. The diffusion filter allows a gas to diffuse into and out of a chamber formed in the tube between the platform and the diffusion filter. The platform is typically a printed circuit board, on which optical and electrical systems are mounted, and the diffusion filter is typically a sintered metal and/or plastic fiber filter. The diffusion filter and the platform can be attached to the tube to create an explosion-proof chamber capable of containing an explosion within the chamber.

The optical system typically includes an infrared source, a curved mirror on the inner wall of the tube, and a detector assembly. The curved mirror directs and focuses light from the infrared source onto the detector assembly. The detector assembly receives the infrared light reflected by the mirror and determines the amount of light absorbed by the gas in the tube. Coating a reflecting material on or polishing a portion of the inner wall of the tube can form the mirror in the sensor. The infrared source is typically a miniature light bulb.

The gas sensor may further include a partition between the infrared source and the detector assembly, a removable filter, connecting pins attached to the platform, and a sealing layer formed under the platform. The partition reduces cross-talk or direct transmission between the infrared source and the detector assembly and thereby increases the optical path length through the gas sample to the detector assembly. The connecting pins provide electrical communications between the gas sensor and an external system.

In one embodiment, the detector assembly includes a signal detector and a reference detector. The signal detector uses a first bandpass interference filter that passes a specific wavelength range of the infrared light into the signal detector. The wavelength range of the first bandpass interference filter corresponds to a characteristic absorption wavelength of a target gas for the sensor. The reference detector uses a second bandpass interference filter that passes a wavelength range that the target gas does not absorb. The detector assembly may include multiple signal detectors and a single reference detector or multiple signal and reference detectors to detect multiple gases simultaneously.

BRIEF DESCRIPTION OF THE DRAWINGS

Use of the same reference symbols in different figures indicates similar or identical items.

DETAILED DESCRIPTION OF THE INVENTION

An aspect of the present invention is to provide an explosion-proof NDIR sensor, so that NDIR sensors can be used where explosive gases may be present, for example, in the underground tunnels and sewers, chemical plants, and oil refineries. This gas sensor is compact and has no moving parts, superior gas detection sensitivity, long-term stability, low power consumption, and low manufacturing cost.

Figure 1:
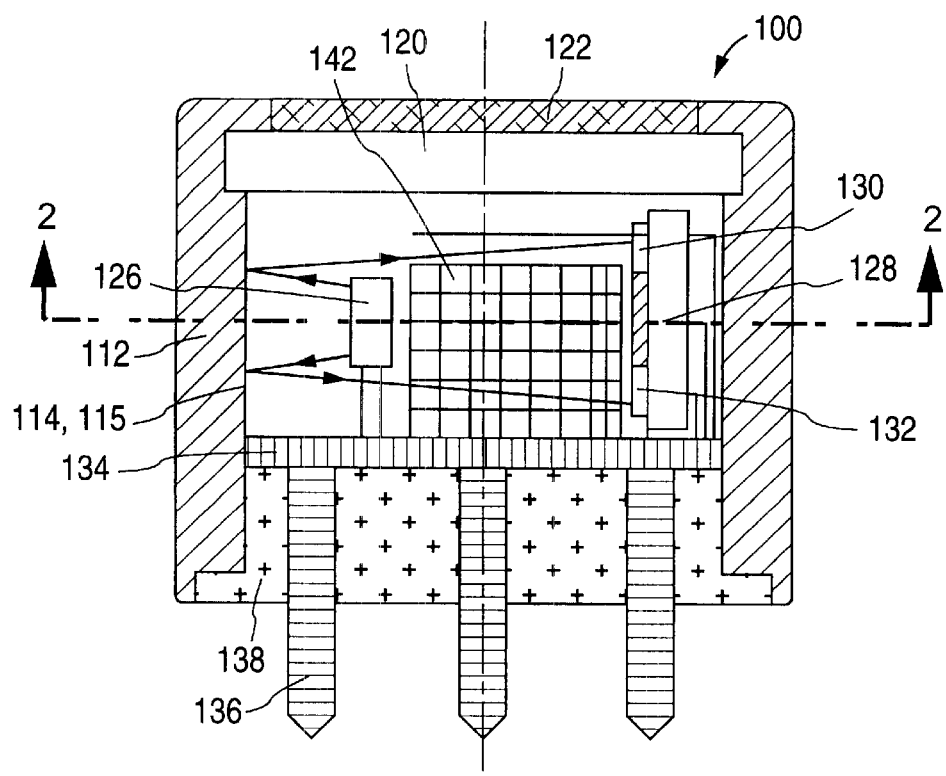
FIG. 1 is a sectional view of an explosion-proof single-gas NDIR sensor in accordance with an embodiment of the present invention.
Figure 2:
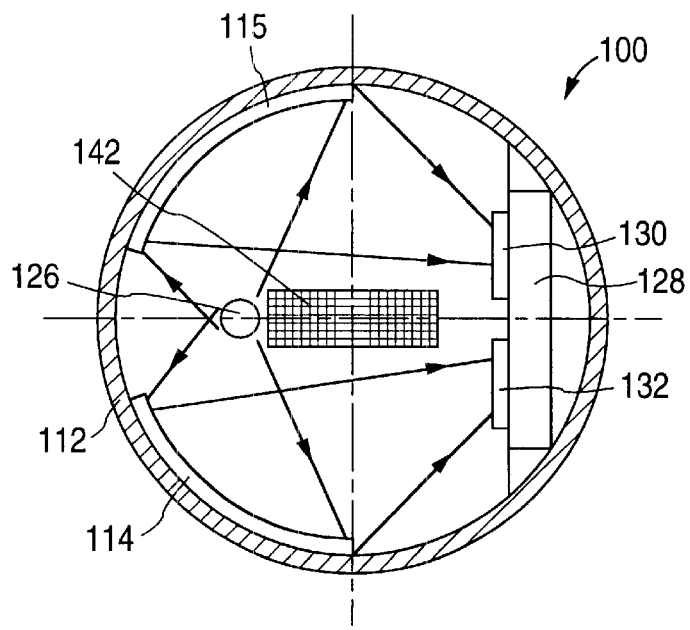
FIG. 2 is a schematic top view of the explosion-proof single-gas NDIR sensor of FIG. 1.

FIG. 1 is a cross-sectional side view of an explosion-proof single-gas NDIR sensor 100 in accordance with an embodiment of the present invention. FIG. 2 is a top view of sensor 100 cut along the line 2—2 of FIG. 1. Sensor 100 includes a platform 134, an infrared source 126, a partition structure 142, a detector assembly 128, and a metallic tube 112. Tube 112 surrounds platform 134. An exemplary metallic tube 112 is cylindrical and made of 0.125" thick stainless steel or 2024 aluminum alloy, and the height and outer diameter of metallic cylindrical tube 112 is respectively 0.75" and 1.00". Portions of the inner wall of metallic cylindrical tube 112 are made highly reflective by polishing the inner wall or coating a reflective material on the inner wall. These highly reflective portions of the inner wall of metallic cylindrical tube 112 form cylindrical mirrors 114 and 115. A known chemical or mechanical polishing process can be used to form cylindrical mirrors 114 and 115. Additional gold or nickel coating applied after polishing may improve the reflectivity of mirrors 114 and 115.

Platform 134 can be a printed circuit board on which infrared source 126, partition structure 142, and detector assembly 128 are mounted, for example by soldering. Infrared source 126 can be a miniature light bulb because such miniature light bulbs are durable (more than five years lifetime), inexpensive and can be pulsed at low frequencies (1–10 Hz.) with excellent contrast. The electrical pulsing makes infrared source 126 modulated. Other industry standard infrared sources including miniature Nernst glowers and laser diodes can be also used for infrared source 126.

Detector assembly 128 includes a signal detector 132 and a reference detector 130, both of which can either be thermopile or pyroelectric detectors. A typical thermopile detector is made of multiple polycrystalline silicon thermoelements packaged in a standard TO-5 package (0.24" in diameter and 0.12" in height). A typical pyroelectric detector is made of pyroelectric materials packaged in the same TO-5 package. Signal detector 132 measures the intensity of infrared light at the wavelengths associated with the absorption spectrum of a target gas to be detected or measured.

Signal detector 132 has a narrow bandpass interference filter (not shown), which is a window that hermetically seals the TO-5 package of signal detector 132. Reference detector 130 has another narrow bandpass interference filter (not shown), which is a window that hermetically seals the TO-5 package of reference detector 130.

The narrow bandpass interference filters only transmit the light having wavelengths in a narrow range surrounding their center wavelength (CWL), and keep all other wavelengths of the light from arriving at detectors 130 and 132. In other words, each of the narrow bandpass filters filter out any light having wavelengths longer or shorter than its own CWL. Typically, narrow bandpass filters, which are 0.02" thick and have an area of 0.08"×0.08", are attached on the top of the TO-5 metal can, so that the distance between the narrow bandpass filters and detectors 130 and 132 is 0.02".

The narrow bandpass interference filter for signal detector 132 passes only the infrared radiation in a first center wavelength band corresponding to an absorption peak in the spectrum of the target gas. The narrow bandpass interference filter for reference detector 130 passes infrared radiation in a second center wavelength band that is not absorbed by gases found in the gas sample. An output signal from signal detector 132 indicates the intensity of received infrared light in the first center wavelength band.

An exemplary narrow bandpass interference filter includes a number of dielectric layers formed on a substrate. For example, silicon dioxide layers are deposited on a silicon substrate. The thickness or the number of the dielectric layers determines the transmission characteristics of the narrow bandpass filter, that is, the CWL of the filter. A narrow bandpass filter having CWL of about 3.80 to 4.00 $\mu$m is typically used for reference detector 130. Narrow bandpass filters having CWL of about 3.40 $\mu$m, 4.26 $\mu$m, 4.64 $\mu$m, and 5.30 $\mu$m are used for signal detector 132 in detecting hydrocarbons (HC), carbon dioxide ($CO_2$), carbon monoxide (CO), and nitrogen monoxide (NO), respectively.

The concentration C of target gas in a gas sample is calculated by a method well-known for NDIR detectors. In particular, a drop ΔUa in the output signal Ua of signal detector 132 is proportional to the infrared light intensity and the concentration C of the target gas in a sample. Equation 1 gives the target gas concentration C determined from a drop ΔUa in the signal from detector 130.

$$C=C0*(\Delta Ua/\Delta Ua0)*(Ub/Ub0) \qquad \text{Equation 1:}$$

In Equation 1, ΔUaO indicates a drop in the signal from signal detector 132 achieved during a calibration measurement when a known gas concentration C0 of the target gas is present in sensor 100. Ub and Ub0 are the signal values from reference detector 130 during the measurement and calibration, respectively. Equation 2 indicates the drop ΔUa in terms of signal values Ua and Ub from respective detectors 132 and 130.

$$\Delta Ua=Ub*K-Ua \qquad \text{Equation 2:}$$

In Equation 2, K is a constant that is equal to the ratio of the signal levels from detectors 132 and 130 when the concentration of the target gas in sensor 100 is zero. The constant K is equal to 1 if detectors 130 and 132 provide equal signals in the absence of the target gas.

Partition structure 142 blocks or minimizes the direct transmission of infrared light from infrared source 126 to detector assembly 128, thereby increasing the optical path length between infrared source 126 and detector assembly 128 and improving the overall signalto-noise ratio of sensor 100. Partition structure 142 can be made of any material that is opaque to or reflective of infrared light. A piece of stainless steel is suitable for partition structure 142. Partition structure 142 further serves to define the pathlength of the radiation from infrared source 126 by suppressing stray light from reaching detectors 130 and 132.

Infrared source 126, detector assembly 128, partition structure 142, and cylindrical mirrors 114 and 115 form an optical system for sensor 100. Cylindrical mirrors 114 and 115 reflect and focus the radiation or light from infrared source 126 onto signal and reference detectors 132 and 130, respectively, of detector assembly 128. While traveling inside sensor 100, the infrared light, which has a spectrum of wavelengths, is partially absorbed if the target gas is present in sensor 100. In particular, the target gas absorbs the light at the specific wavelength that signal detector 132 measures.

In an exemplary geometry for sensor 100, infrared source 126 is one half of a radius from the center of tube 112. Detector assembly 128 is perpendicular to a diameter that intersects infrared source 126 and is at ⅔ of the radius from the center of tube 112 on the side opposite infrared source 126. Partition structure 142 is at the center of tube 112, extending toward both infrared source 126 and detector assembly 128 by the distance of about ⅓ radius of tube 112. The radius of curvature of cylindrical mirrors 114 and 115 is similar to the radius of tube 112.

Sensor 100 further includes a sintered metal filter 120 and a removable plastic fiber filter 122. Sintered metal filter 120 is a porous sintered metal plate and joined to the top of metallic tube 112. Sintered metal filter 120 is typically at least 0.08" thick and made by sintering stainless steel power having a particle size up to 100 μm. A typical porosity content of sintered metal filter 120 is 10 to 30%, and the size of pores is about 10 to 40 μm. Sintered metal filter 120 permits diffusion, serves as a dust filter, and inhibits the escape of any gases ignited inside sensor 100. A typical thickness of sintered metal filter 120 is about 0.125", which provides the explosion-proof capability and structural integrity in sensor 100.

A known close-fit pressing fabricates sintered metal filter 120 and simultaneously joins sintered metal filter 120 to tube 112. The fabrication and joining begins with filling stainless steel metal powders, which is mixed with a binder, into a cavity that is at the top end of tube 112. Then, the stainless steel metal powders are pressed into the shape of sintered metal filter 120 and temporarily joining to tube 112. The pressed powders shaped and joined to tube 112 are sintered in a positive-pressure hydrogen furnace at about the melting point of the powders. The hydrogen environment prevents oxide film formation of the powers during the sintering. Sintering results in a sintered metal filter 120 that is strong and permanently joined to tube 112.

Removable plastic fiber filter 122 covers sintered metal filter 120 and serves as a semi-permeable membrane that allows the gas molecules to enter and leave sensor 100 by diffusion along a direction perpendicular to removable plastic fiber filter 122. PTFE or Cellulose filter having pores less than 1 μm diameter can be used as plastic fiber filter 122. Removable plastic fiber filter 122 extends the lifetime of sintered metal filter 120 by filtering out dust from the gas sample before the dust enters sintered metal filter 120.

In an exemplary embodiment, infrared source 126, partition structure 142, and detector assembly 128 are mounted on platform 134, which is a printed circuit board. When platform 134 is a printed circuit board, signal preconditioning circuit elements (not shown) can be easily mounted on platform 134 for processing signals from detectors 130 and 132. For example, preamplifiers can be mounted on the platform close to detectors 130 and 132 to boost the signal-to-noise ratio of the output signal. This is particularly advantageous when detectors 130 and 132 are thermopile detectors, which have output signal amplitude as low as a few microvolts. The preconditioning circuit can further include sensors of temperature (e.g., thermosistors), humidity, and pressure and circuitry that adjusts the output signal according to changes in the ambient air. Such circuitry improves the accuracy of the measurement since IR absorption depends on temperature, humidity, and pressure in the sample gas.

Figure 3:
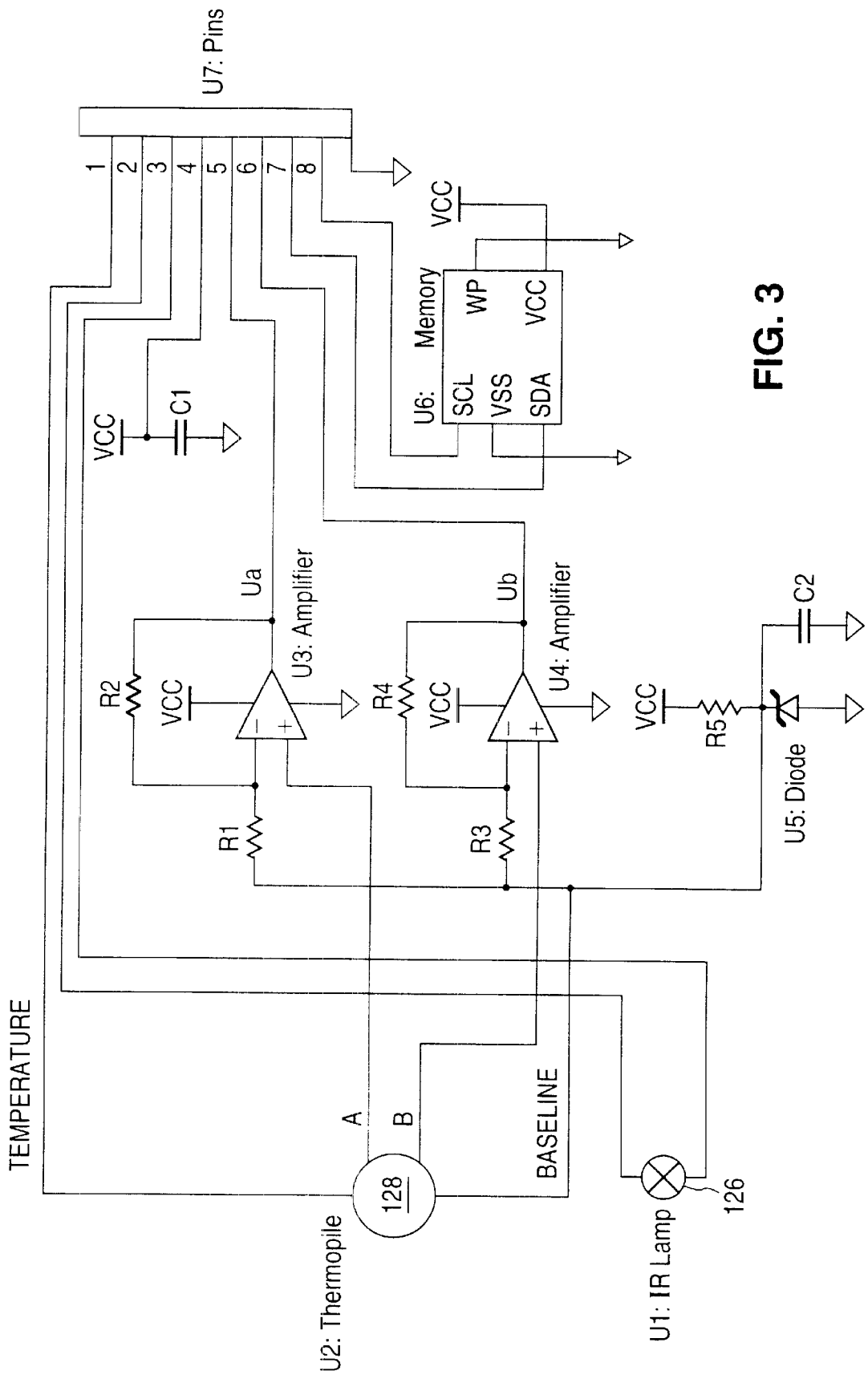
FIG. 3 is a schematic of signal conditioning circuit mounted on a platform in the sensor of FIG. 1.

FIG. 3 is a circuit diagram of signal conditioning circuit on a printed circuit board portion of platform 134. The circuit includes an infrared lamp U1, a thermopile U2, amplifiers U3 and U4, a memory U6, and I/O pins U7, all of which are mounted on the printed circuit board. Lamp U1 is the source of infrared light (e.g., source 126 in FIG. 1). Thermopile U2 is a portion of detector assembly 128 and provides output signals A and B indicating the intensity of infrared light that signal detector 132 and reference detector 134 measure and a reference signal BASELINE for interpretations of signals A and B. Amplifiers U3 and U4 are differential amplifiers that amplify the differences between reference signal BASELINE and signals A and B to generate signals Ua and Ub. A temperature sensor provides a signal TEMPERATURE indicating the temperature of the sample gas. Additional sensors can provide humidity and pressure information.

Signals Ua, Ub, and TEMPERATURE are output through pins U7 (e.g., pins 136 of FIG. 1) to an external system (not shown) for calculation of the concentration of the target gas in the sample. The external system can include a signal processor or a computer system that executes software for concentration calculations. Memory U6 is a non-volatile memory integrated circuit such as a serial EEPROM that stores calibration information for the sensor. In particular, the manufacturer or a user stores calibration information in memory U6 during a calibration process, and the external system accesses the information from memory U6 for calculations of the target gas concentrations during measurements.

Returning to FIG. 1, connecting pins 136 under platform 134 provide the electrical communications between sensor 100 and the external system. Connecting pins 136 can be soldered onto platform 134. In addition, an epoxy layer 138, which is the bottom cap of sensor 100, seals and attaches platform 134 and tube 112. The thickness of epoxy layer 138 is typically more than 0.12" to make sensor 100 explosion-proof.

Figure 4:
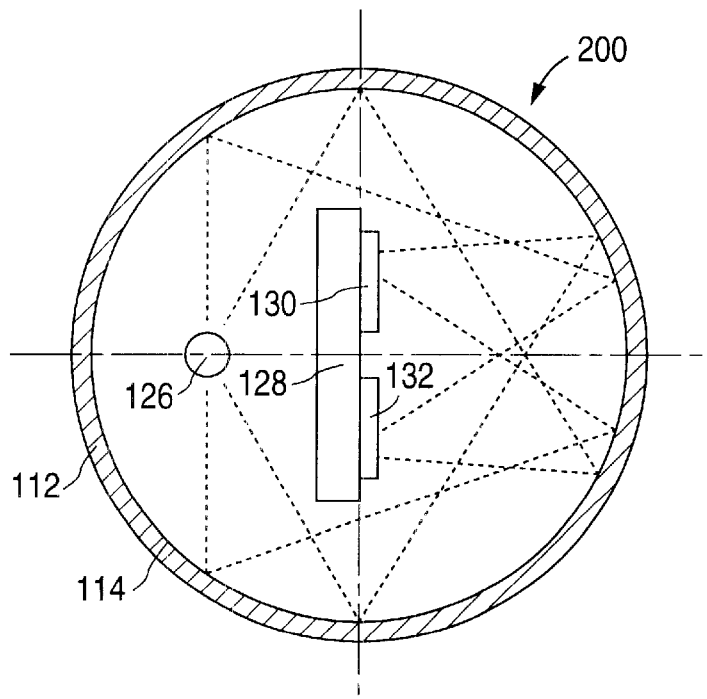
FIG. 4 is a schematic top view of an explosion-proof single-gas NDIR sensor in accordance with another embodiment of the present invention.

FIG. 4 illustrates an explosion-proof single-gas NDIR sensor 200 in accordance with another embodiment of the present invention. Sensor 200 is identical to sensor 100 of FIG. 2 except for the configuration of the optical system. The optical path length from the infrared source 126 to detectors 130 and 132 in sensor 200 is longer than that in sensor 100.

In sensor 200, detector assembly 128 is located at the center of cylindrical tube 112. Infrared source 126 is located behind detector assembly 128, so that the light from infrared source 126 reflects twice from the inner wall of tube 112 before arriving at detector assembly 128. Thus, the location and size of cylindrical mirrors 114 and 115 are changed. For example, the whole inner wall of cylindrical tube 112 may be a mirrored surface forming both cylindrical mirrors 114 and 115. Sensor 200 does not require a partition structure because the back of detector assembly 128 blocks cross-talk between infrared source 126 and detectors 130 and 132.

Figure 5:
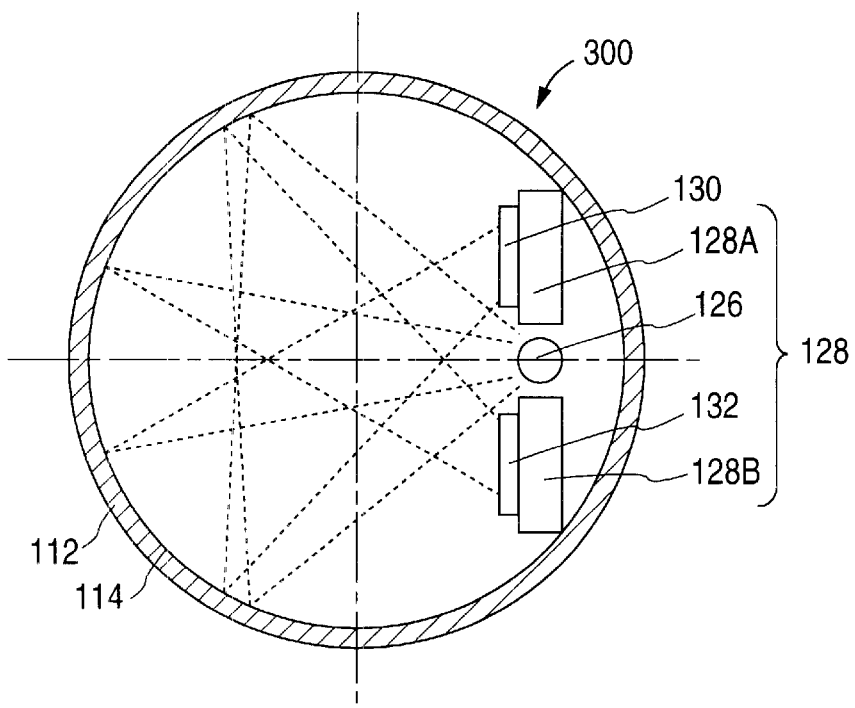
FIG. 5 is a schematic top view of an explosion-proof single-gas NDIR sensor in accordance with still another embodiment of the present invention.

FIG. 5 illustrates an explosion-proof single-gas NDIR sensor 300 in accordance with still another embodiment of the present invention. Sensor 300 is another variation of sensor 100 of FIG. 2. In sensor 300, the optical system, which includes detector assemblies 128A and 128B, infrared source 126, and cylindrical mirror 114 has yet another configuration. The optical path length from the infrared source in sensor 300 is longer than that in sensor 100.

In sensor 300, a detector assembly 128 is divided into two pieces 128A and 128B. Detector assembly 128A includes reference detector 130, and detector assembly 128B includes signal detector 132. Infrared source 126 is between detector assemblies 128A and 128B, so that the light from infrared source 126 reflects once or twice from mirror 114 before arriving at detector assemblies 128A and 128B. Sensor 300 does not require a partition structure because detector assemblies 128A and 128B block direct transmission of light from infrared source 126 to detectors 130 and 132.

The NDIR sensors described above in accordance with embodiments of the present invention are single-gas gas sensors that have a single signal detector that measures wavelengths corresponding to a single target gas. Alternatively, a multi-gas NDIR sensor can include multiple signal detectors that measure different wavelength bands and detect two or more gases simultaneously in real time. The multi-gas NDIR sensors can be constructed by installing multiple signal detectors and a single reference detector or multiple detector assemblies.

Explosion-proof gas sensors that can be used in the presence of flammable gas should be constructed such that gas-explosions occurring within the sensors do not ignite the flammable gas outside the sensors. In other words, the enclosure of the sensor is required to withstand the inner explosions without bursting or loosening of joints. The enclosure of the NDIR sensors according to the embodiments of the present invention, which includes tube, epoxy layer, and sintered metal filter, provides the explosion-proof property. The enclosure is constructed in accordance with the description of industrial standards such as Underwriters Laboratories 913. For example, the stainless steel tube is at least 0.08" thick, the sintered metal filter is also at least 0.08" thick, and the epoxy is at least 0.12" thick.

In accordance with the exemplary embodiments of the present invention, the NDIR sensors are explosion-proof, compact, rugged, fast responding, and have high gas detection sensitivity, long-term stability, and low manufacturing cost. The sensors lengthen and define the optical path of the light from infrared source using an optimum design of the cost-effective optical system, which includes an infrared source, cylindrical mirrors, and a detector assembly. The cylindrical mirrors focus light from the source at the detectors to improve energy efficiency.

Although the invention has been described with reference to particular embodiments, the description is only an example of the invention's application and should not be taken as limiting. Various adaptations and combinations of features of the embodiments disclosed are within the scope of the invention as defined by the following claims.

We claim:

1. A gas sensor comprising:

a tube having an inner wall that includes a reflective portion;

a platform in a first end of the tube;

a filter in a second end of the tube, wherein the filter allows gas to enter through the filter into the tube;

an infrared source on the platform; and a detector assembly on the platform and positioned to receive infrared light from the infrared source after reflection from the reflective portion of the inner wall.

2. The gas sensor of claim 1, further comprising a partition between the infrared source and the detector assembly to block direct transmission of infrared light from the infrared source to the detector assembly.

3. The gas sensor of claim 1, wherein the filter comprises a fixed filter and a removable filter.

4. The gas sensor of claim 3, wherein the removable filter comprises a plastic fiber filter.

5. The gas sensor of claim 3, wherein the fixed filter is made of a porous sintered metal plate.

6. The gas sensor of claim 1, wherein the filter comprises a porous sintered metal plate.

7. The gas sensor of claim 6, wherein the porous sintered metal plate comprises sintered stainless steel.

8. The gas sensor of claim 7, wherein the sintered stainless steel is at least 0.08" thick.

9. The gas sensor of claim 1, further comprising connecting pins attached to the platform, the connecting pins providing electrical communication between the detector assembly and an external system.

10. The gas sensor of claim 1, further comprising a sealing layer formed under and supporting the platform.

11. The gas sensor of claim 10, wherein the sealing layer is made of an epoxy resin.

12. The gas sensor of claim 11, wherein the epoxy sealing layer is at least 0.12" thick.

13. The gas sensor of claim 1, wherein the tube is made of a metal.

14. The gas sensor of claim 13, wherein the metal is selected from the group consisting of a stainless steel and an aluminum alloy.

15. The gas sensor of claim 14, wherein the stainless steel tube is at least 0.08" thick.

16. The gas sensor of claim 1, wherein the reflective portion is a polished portion of the inner wall of the tube.

17. The gas sensor of claim 1, wherein the reflective portion comprises a coating of a reflecting material on the inner wall of the tube.

18. The gas sensor of claim 1, wherein the platform is a printed circuit board.

19. The gas sensor of claim 18, further comprising a signal conditioning circuit formed on the printed circuit board.

20. The gas sensor of claim 19, wherein the detector assembly comprises a thermopile detector and the signal conditioning circuit comprises an amplifier coupled to amplify a signal from the thermopile detector, the amplifier be adjacent to the thermopile detector on the printed circuit board.

21. The gas sensor of claim 1, wherein the infrared source is a light bulb.

22. The gas sensor of claim 1, wherein the detector assembly comprises a signal detector and a reference detector.

23. The gas sensor of claim 22, wherein the signal and reference detectors are thermopile detectors.

24. The gas sensor of claim 22, wherein the signal and reference detectors are pyroelectric detectors.

25. The gas sensor of claim 22, wherein a first bandpass filter is on the signal detector, the first bandpass filter allowing a first wavelength range of light to pass through the first bandpass filter, wherein a target gas absorbs light in the first wavelength range.

26. The gas sensor of claim 25, wherein a center wavelength of the first bandpass filter is 3.40 $\mu$m when the target gas is a hydrocarbon.

27. The gas sensor of claim 25, wherein a center wavelength of the first bandpass filter is 4.26 $\mu$m when the target gas is carbon dioxide.

28. The gas sensor of claim 25, wherein a center wavelength of the first bandpass filter is 4.64 $\mu$m when the target gas is carbon monoxide.

29. The gas sensor of claim 25, wherein a center wavelength of the first bandpass filter is 5.30 $\mu$m when the target gas is an oxide of nitrogen.

30. The gas sensor of claim 25, wherein a second bandpass filter is on the reference detector, the second bandpass filter allowing a second wavelength range of light to pass through the second bandpass filter, wherein the target gas does not absorb light in the second wavelength range.

31. The gas sensor of claim 30, wherein a center wavelength of the second bandpass filter is between 3.80 $\mu$m and 4.00 $\mu$m inclusively.

32. The gas sensor of claim 1, wherein the reflective portion includes all of the inner wall of the tube.

33. The gas sensor of claim 1, wherein the gas sensor is explosion-proof.

34. The gas sensor of claim 1, further comprising means for sealing the first and second ends of the tube to make the gas sensor explosion-proof.

35. The gas sensor of claim 34, where the means for sealing comprising:

a permanent joint attaching the filter to the tube; and a sealing layer under the platform, wherein the filter, the tube, and the sealing are sufficiently strong to contain an explosion inside the gas sensor.

36. The gas sensor of claim 1, wherein the platform and the filter are attached to the tube to provide a chamber that confines any ignited gas within the chamber.

37. The gas sensor of claim 1, wherein the detector assembly comprises a plurality of signal detectors and a reference detector.

38. The gas sensor of claim 1, wherein the detector assembly comprises a plurality of pairs of signal and reference detector.

39. An explosion-proof gas sensor comprising:

a tube having an inner wall that includes a reflective portion;

a platform in a first end of the tube;

a filter in a second end of the tube, wherein the filter allows gas to enter through the filter into the tube;

an infrared source on the platform; and a detector assembly on the platform and positioned to receive infrared light from the infrared source after reflection from the reflective portion of the inner wall;

wherein the first end of the tube and the second end of the tube are connected to the tube such that an explosion that occurs within the tube is confined within the tube.

40. The explosion-proof gas sensor of claim 39, wherein the filter includes a fixed filter made of a porous sintered metal plate.

41. The explosion-proof gas sensor of claim 40, wherein the porous sintered metal plate comprises sintered stainless steel.

42. The explosion-proof gas sensor of claim 40, wherein the porous sintered metal plate is at least 0.08" thick.

43. The explosion-proof gas sensor of claim 40, further comprising a sealing layer formed under and supporting the platform.

44. The explosion-proof gas sensor of claim 43, wherein the sealing layer is made of an epoxy resin.

45. The explosion-proof gas sensor of claim 43, wherein the sealing layer is at least 0.12" thick.

46. The explosion-proof gas sensor of claim 39, wherein the tube is made of a metal that is at least 0.08" thick.

* * * * *